United States Patent
Douseki et al.

(10) Patent No.: US 12,245,923 B2
(45) Date of Patent: Mar. 11, 2025

(54) POWER GENERATION SENSOR

(71) Applicants: The Ritsumeikan Trust, Kyoto (JP); ABLIC Inc., Nagano (JP)

(72) Inventors: Takakuni Douseki, Shiga (JP); Ami Tanaka, Shiga (JP); Shiyuya Imoto, Shiga (JP); Fumiyasu Utsunomiya, Nagano (JP)

(73) Assignees: The Ritsumeikan Trust, Kyoto (JP); ABLIC Inc., Nagano (JP)

( * ) Notice: Subject to any disclaimer, the term of this patent is extended or adjusted under 35 U.S.C. 154(b) by 112 days.

(21) Appl. No.: 18/331,151

(22) Filed: Jun. 7, 2023

(65) Prior Publication Data
US 2024/0004099 A1   Jan. 4, 2024

(30) Foreign Application Priority Data
Jun. 29, 2022 (JP) .................. 2022-104641

(51) Int. Cl.
| | | |
|---|---|---|
| *A61F 13/42* | (2006.01) | |
| *A61F 13/49* | (2006.01) | |
| *G01D 11/24* | (2006.01) | |
| *G01V 3/00* | (2006.01) | |
| *G01V 3/08* | (2006.01) | |

(52) U.S. Cl.
CPC .............. *A61F 13/42* (2013.01); *A61F 13/49* (2013.01); *G01V 3/088* (2013.01); *G01D 11/245* (2013.01); *G01V 3/00* (2013.01)

(58) Field of Classification Search
CPC ....... G01D 11/245; A61F 13/42; A61F 13/49; G01N 33/48785; G01N 33/493; G01V 3/00; G01V 3/088; G01M 3/16; H02N 3/00
See application file for complete search history.

(56) References Cited

FOREIGN PATENT DOCUMENTS

| JP | 2015229003 | | 12/2015 | | |
| JP | 2017032331 | A * | 2/2017 | | |
| JP | 2019141190 | A * | 8/2019 | | |
| WO | WO-2013061963 | A1 * | 5/2013 | ............. | A61F 13/42 |

\* cited by examiner

*Primary Examiner* — Amy He
(74) *Attorney, Agent, or Firm* — JCIPRNET

(57) ABSTRACT

A power generation sensor, generating electric power using a liquid, includes: a base; a positive electrode for power generation disposed in a first direction of the base and containing a first material; a negative electrode for power generation disposed in the first direction and containing a second material; a first connector electrode connected to a one-side end of the positive electrode in the first direction and to a sensor module; and a second connector electrode connected to a one-side end of the negative electrode in the first direction and to the sensor module. The first connector electrode contains the first material and has a larger width in a second direction orthogonal to the first direction than the positive electrode in the second direction. The second connector electrode contains the second material and has a larger width in the second direction than the negative electrode in the second direction.

3 Claims, 10 Drawing Sheets

POWER GENERATION SENSOR

CROSS-REFERENCE TO RELATED APPLICATION

This application claims the priority benefits of Japanese application no. 2022-104641, filed on Jun. 29, 2022. The entirety of each of the above-mentioned patent applications is hereby incorporated by reference herein and made a part of this specification.

BACKGROUND

Technical Field

The present invention relates to a power generation sensor.

Description of Related Art

Japanese Patent Laid-Open No. 2015-229003 discloses a power generation module including an electrode generating an electromotive force in accordance with contact with urine. Such a power generation module can be used as a power generation sensor.

In a power generation sensor, there is a request for easy positioning performed when a module receiving generated electric power is connected to a power generation electrode. For example, a case in which a module is connected to a power generation electrode mounted in a member such as a diaper attached to a human body is assumed.

SUMMARY

The present invention provides a power generation sensor enabling easy positioning at the time of connecting a module receiving generated electric power to a power generation electrode.

According to an embodiment of the present invention, a power generation sensor generating electric power using a liquid includes: a base; a positive electrode for power generation disposed in a first direction of the base and composed of a first material; a negative electrode for power generation disposed in the first direction of the base and composed of a second material; a first connector electrode connected to a one-side end of the positive electrode in the first direction and connected to a sensor module; and a second connector electrode connected to a one-side end of the negative electrode in the first direction and connected to the sensor module, in which the first connector electrode is composed of the first material and has a width in a second direction orthogonal to the first direction larger than a width of the positive electrode in the second direction, and the second connector electrode is composed of the second material and has a width in the second direction larger than a width of the negative electrode in the second direction.

According to the present invention, by configuring widths of the first connector electrode and the second connector electrode to be larger than widths of the positive electrode and the negative electrode, positioning at the time of connection to the sensor module can be more easily performed than in a case in which the widths of the first and second connector electrodes are the same as the widths of the positive electrode and the negative electrode.

DESCRIPTION OF THE EMBODIMENTS

Figure 1:
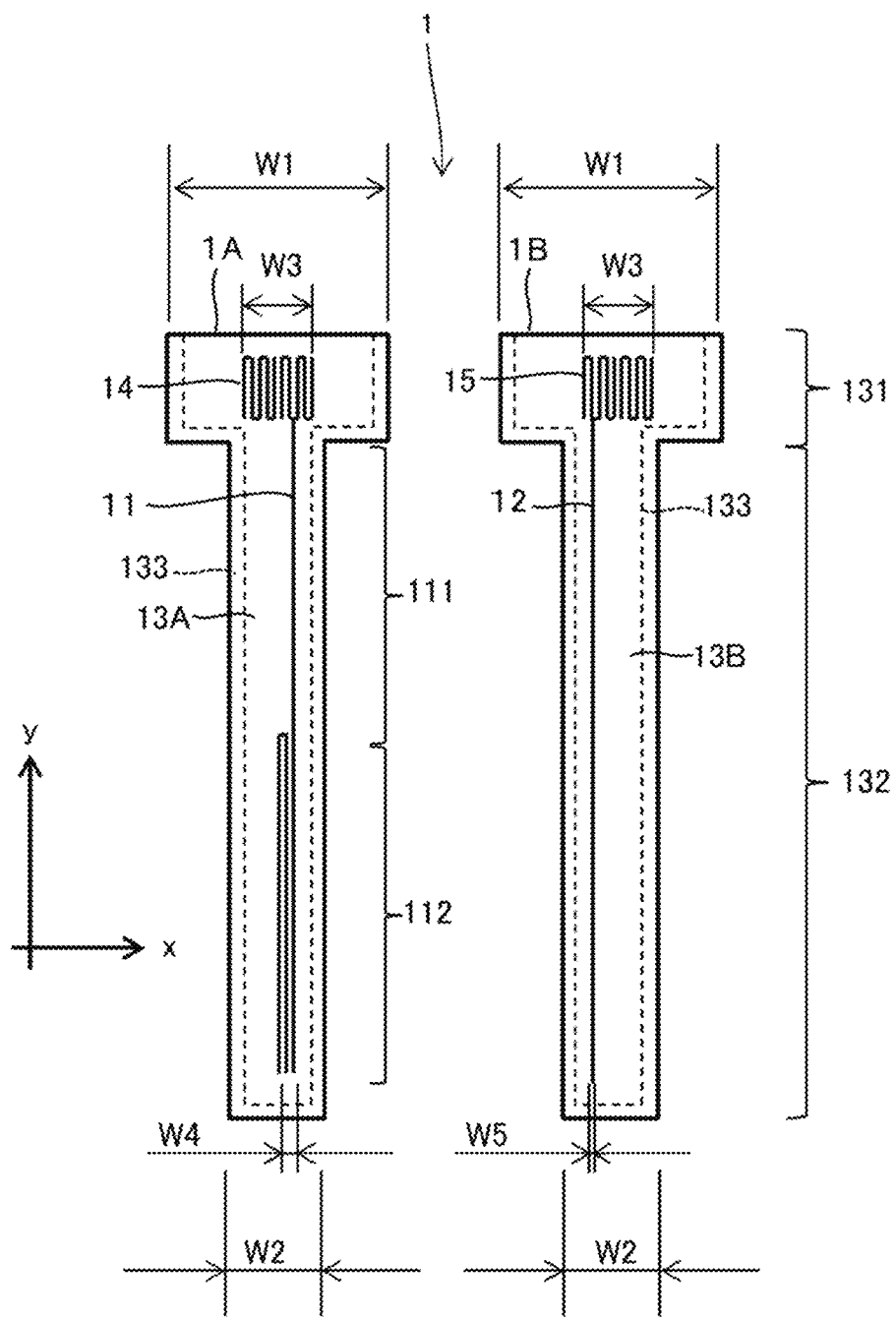
FIG. 1 is a schematic configuration diagram of a sensor according to an embodiment.

Further details will be described in the following embodiment.

(1) A power generation sensor according to an embodiment is a power generation sensor generating electric power using a liquid, the power generation sensor including: a base; a positive electrode for power generation disposed in a first direction of the base and composed of a first material; a negative electrode for power generation disposed in the first direction of the base and composed of a second material; a first connector electrode connected to a one-side end of the positive electrode in the first direction and connected to a sensor module; and a second connector electrode connected to a one-side end of the negative electrode in the first direction and connected to the sensor module, in which the first connector electrode is composed of the first material and has a width in a second direction orthogonal to the first direction larger than a width of the positive electrode in the second direction, and the second connector electrode is composed of the second material and has a width in the second direction larger than a width of the negative electrode in the second direction.

In accordance with the widths of the first connector electrode and the second connector electrode being larger than the widths of the positive electrode and the negative electrode, positioning at the time of connection to a sensor module can be more easily performed than in a case in which the widths of the first and second connector electrodes are the same as the widths of the positive electrode and the negative electrode.

(2) In the power generation sensor of (1), preferably, each of the positive electrode and the negative electrode is composed of a thread having conductivity sewn into the base, and each of the first connector electrode and the second connector electrode is composed of a thread having conductivity sewn into a range of the base wider than the positive electrode and the negative electrode. In accordance with this, similar to the positive electrode and the negative electrode, the first connector electrode and the second connector electrode can be formed by sewing threads having conductivity. In addition, by changing a range of the threads having conductivity sewn to the base, the positive electrode, the negative electrode, and the first connector electrode and the second connector electrode having widths larger than the positive electrode and the negative electrode can be generated. In accordance with this, an electrode material does not need to be cut out and processed, and the electrode material can be used without any waste.

(3) In the power generation sensor of (2), preferably, densities of the threads which compose the first connector electrode and the second connector electrode sewn into the base are higher than densities of the threads which compose the positive electrode and the negative electrode sewn into the base. In accordance with this, positioning at the time of connecting the sensor module to the first connector electrode and the second connector electrode can be easily performed, and connection resistance can be lowered.

In accordance with the widths of the first connector electrode and the second connector electrode being larger than the widths of the positive electrode and the negative electrode, a power generation sensor capable of more easily performing positioning at the time of connection with a sensor module than in a case in which the widths of the first and second connector electrodes are the same as the widths of the positive electrode and the negative electrode can be manufactured.

Figure 2:
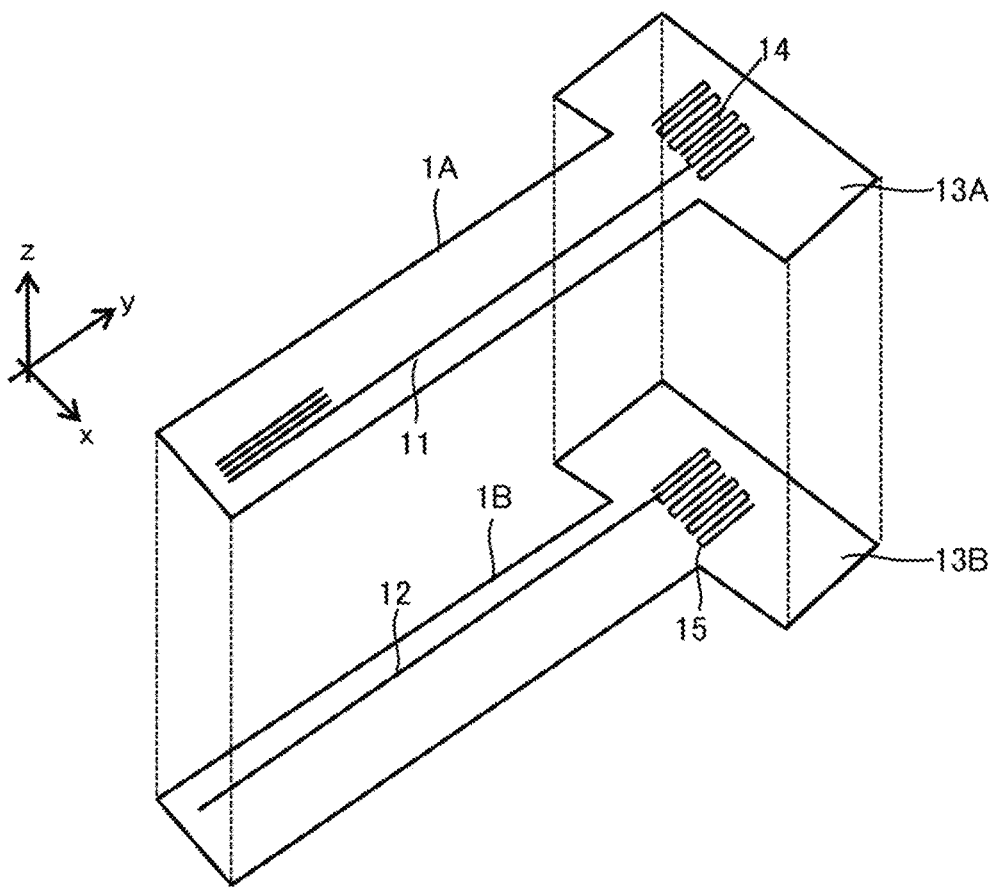
FIG. 2 is a diagram illustrating a method of manufacturing a sensor.
Figure 3:
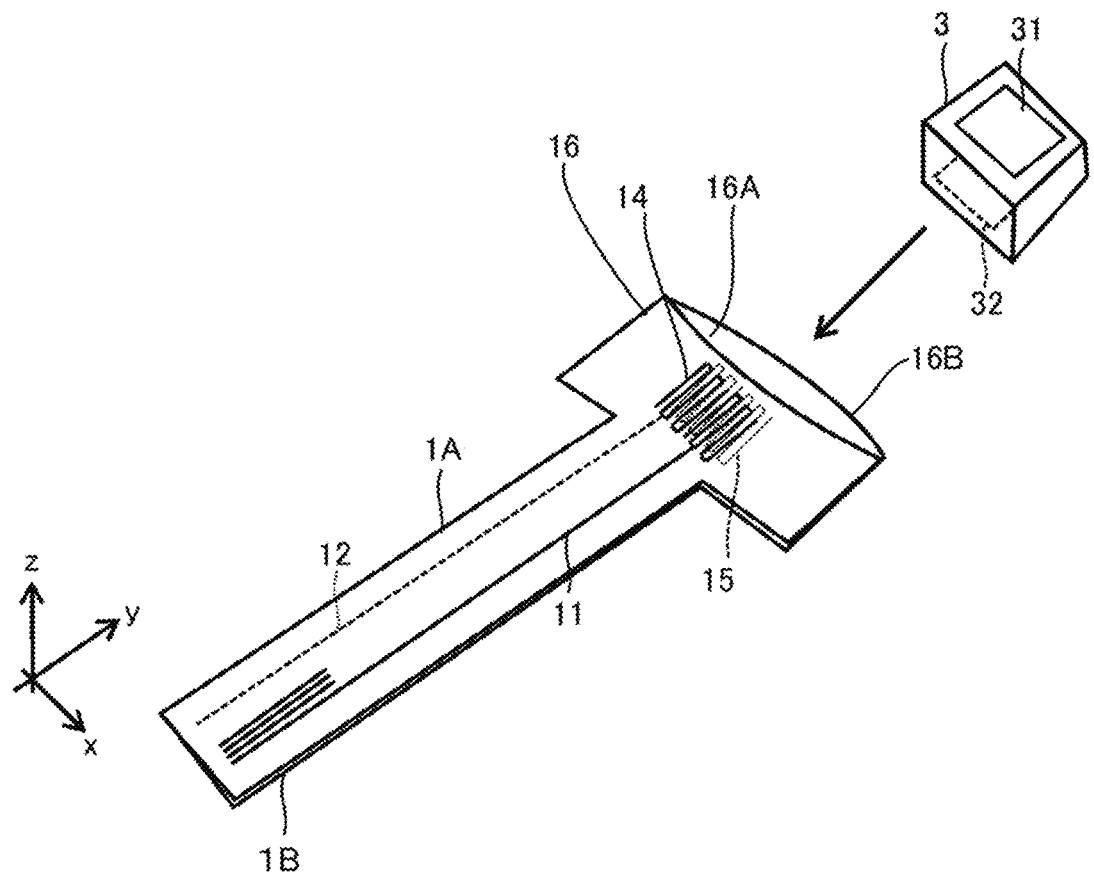
FIG. 3 is a diagram illustrating a method of connecting a module to a sensor.
Figure 4:
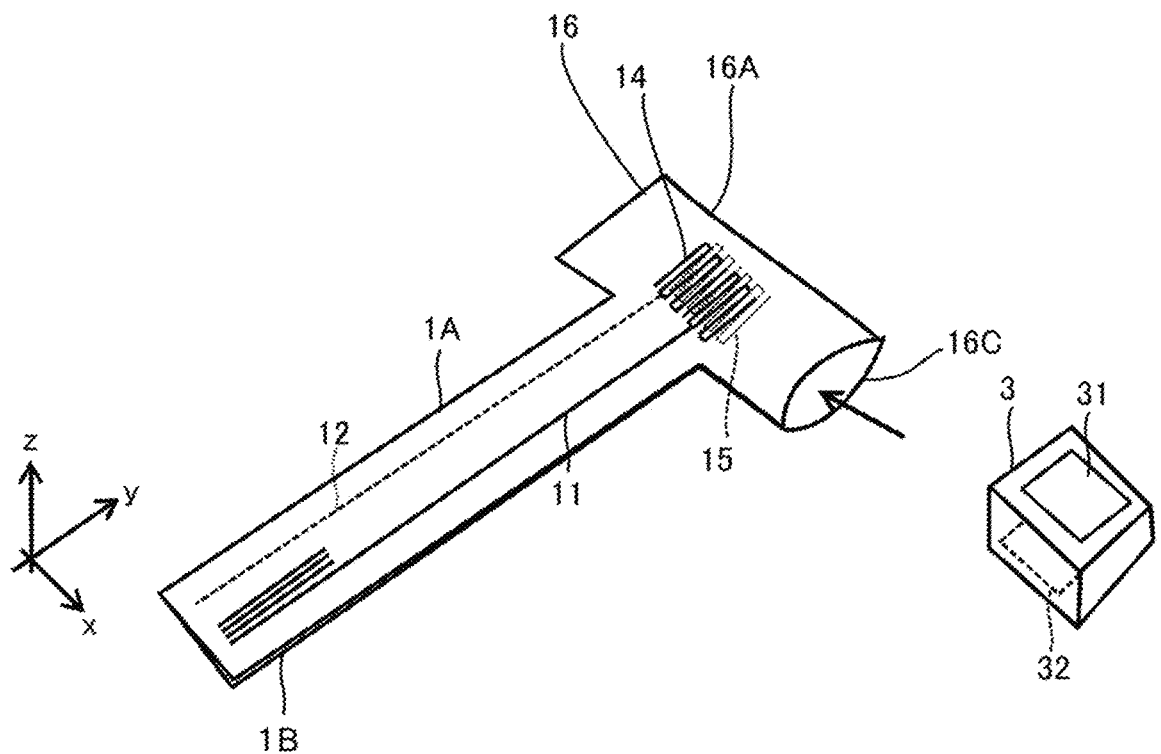
FIG. 4 is a diagram illustrating another example of a method of connecting a module to a sensor.
Figure 5:
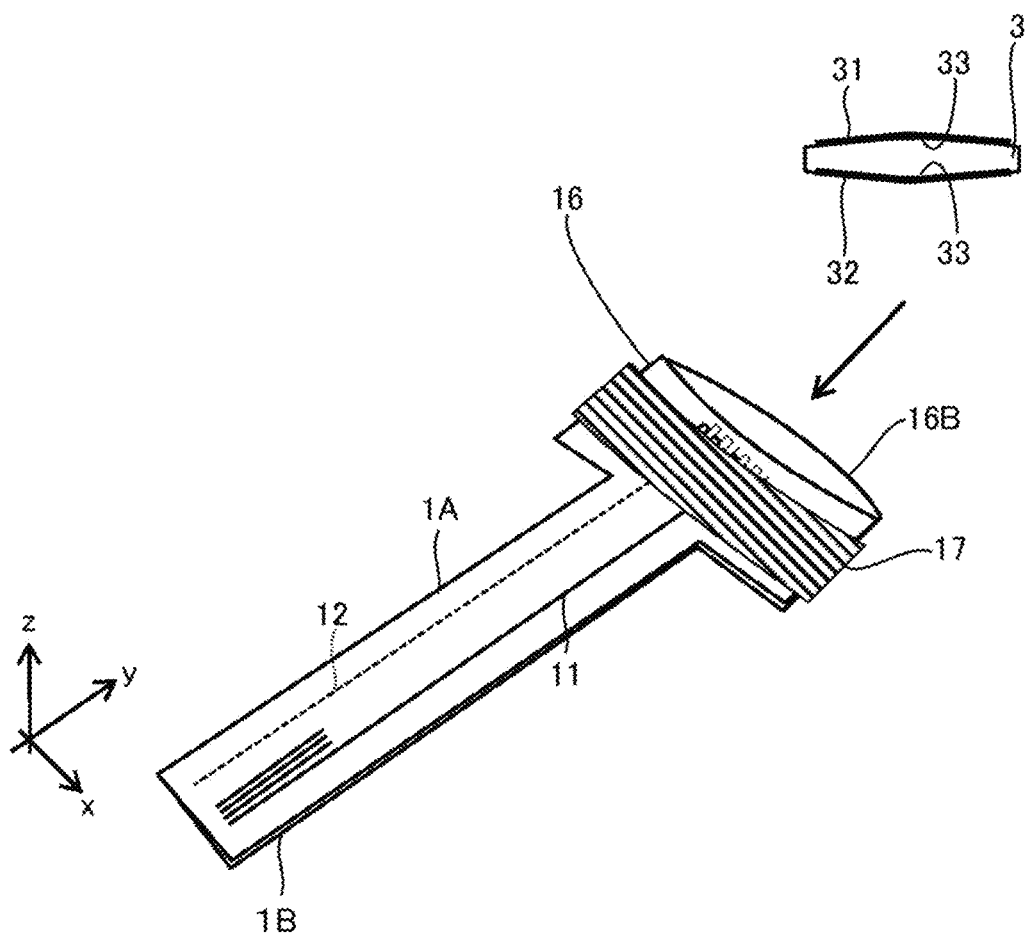
FIG. 5 is a diagram illustrating an example of a contact part.

FIG. 1 is a schematic configuration diagram of a sensor 1 according to this embodiment. FIG. 2 is a diagram illustrating a method of manufacturing the sensor 1. FIG. 3 is a diagram illustrating a method of connecting a module 3 to the sensor 1. FIG. 4 is a diagram illustrating another example of a method of connecting the module 3 to the sensor 1. FIG. 5 is a diagram illustrating an example of a contact part.

The sensor 1 includes a first sensor member 1A and a second sensor member 1B and is configured by overlapping those members. An electrode 11 is disposed in the first sensor member 1A, and an electrode 12 is disposed in the second sensor member 1B. The first sensor member 1A includes a base 13A used for disposing the electrode 11, and the second sensor member 1B includes a base 13B used for disposing the electrode 12.

For example, the bases 13A and 13B are composed of a liquid absorption material. For example, the bases 13A and 13B are fabrics and, for example, are formed of fabrics of a cotton material. The bases 13A and 13B have the same shape or approximately the same shape.

Each of the bases 13A and 13B includes a first base part 131 used for configuring a housing body 16 to be described below and a second base part 132 in which electrodes 11 and 12 are disposed. The second base part 132 is long in one direction and has one end at which the first base part 131 is disposed. With respect to the sensor 1, a length direction of the second base part 132 will be defined as a y axis, and a lateral direction orthogonal to the length direction will be defined as an x axis. The first base part 131 is disposed at an end of the second base part 132 in a positive direction of the y axis.

One pair of electrodes 11 and 12 are electrodes for power generation. The electrode 11 functions as a positive electrode, and the electrode 12 functions as a negative electrode. The electrodes 11 and 12 generate electric power by being brought into contact with a liquid present between the electrodes. In accordance with this, the sensor 1 functions as a power generation sensor and can detect presence of a liquid between the electrodes 11 and 12 in accordance with generated electric power of the electrodes 11 and 12.

The electrodes 11 and 12 are composed of different materials. Each of the electrodes 11 and 12 has a structure of a thread shape or a band shape. As one example, the electrode 11 is composed of a silver thread, and the electrode 12 is composed of an aluminum thread. By configuring the electrodes 11 and 12 using threads, the electrodes 11 and 12 can be easily formed using sewing to be described below. In addition, widths W4 and W5 of the electrodes 11 and 12 in the x-axis direction can be narrowed, and a decrease in the strength can be inhibited. Any material may be used for the electrode 11 as long as it has a structure of a thread shape or a band shape and can serve as a positive electrode, and for example, magnesium, zinc, or iron may be used. Any material may be used for the electrode 12 as long as it has a structure of a thread shape or a band shape and can serve as a negative electrode, and, for example, tin, lead, copper, stainless steel, carbon, gold, or platinum may be used.

The electrodes 11 and 12 are respectively woven into the second base parts 132 of the bases 13A and 13B which are fabrics in the y-axis direction. More specifically, in this example, both of the electrodes 11 and 12 have a thread-shape structure having conductivity, the electrode 11 is woven into the second base part 132 of the base 13A, and the electrode 12 is woven into the second base part 132 of the base 13B.

Preferably at least one of the electrodes 11 and 12 has a surface area of a negative side in the y-axis direction, that is, a rear side, which is larger than a surface area of a positive side in the y-axis direction, that is, a front side. The surface areas represent areas in contact with an absorption body 53 when mounted in an absorption member main body 5 to be described below and represent surface areas of parts of the electrodes 11 and 12 formed using threads, woven into the bases 13A and 13B which are exposed on at least front faces of the bases 13A and 13B on the side of the absorption body 53.

As one example, a first part 111 of the electrode 11 which is a positive side in the y-axis direction, that is, the front side, and a second part 112 which is a negative side in the y-axis direction, that is, the rear side, have different stitch structures of threads with respect to the base 13A. The stich structure represents a structure formed by a thread with respect to a fabric by sewing the thread into the bases 13A and 13B. The stitch structure being different in the first part 111 and the second part 112, for example, represents that a method for sewing the thread forming the electrode 11 is different in the first part 111 and the second part 112. More specifically, in the electrode 11, the second part 112 is sewn into the base 13A using a sewing method for implementing a higher density per unit than the density for the first part 111.

For example, a sewing method having a high density per unit is a sewing method in which an area of a thread which forms the electrode 11 appearing on the front face of the base 13A on the absorption body 53 side is large. For example, the first part 111 is sewn into the base 13A through wave stitching, and the second part 112 is sewn into the base 13A through back-stitching. The back-stitching represents reverse stitching or half-reverse stitching. In accordance with this, in the second part 112, exposure of a thread forming the electrode 11 on the front face of the base 13A is more than exposure in the first part 111.

A length (width) W1 of the first base part 131 of each of the bases 13A and 13B in the x-axis direction is larger than a width W2 of the second base part 132. The first base part 131 forms the housing body 16 in which a module 3 receiving generated electric power is housed. In the housing body 16, the first base parts 131 of the first sensor member 1A and the second sensor member 1B overlapping each other have a space 16A configured therebetween, and the module 3 is housed inside the space 16A.

In the first base parts 131 of the bases 13A and 13B, connector electrodes 14 and 15 are respectively disposed. The connector electrode 14 is connected to a front-side end of the electrode 11 which is one end in the y-axis direction, and the connector electrode 15 is connected to a front-side end of the electrode 12.

The connector electrodes 14 and 15 are respectively composed of the same materials as the electrodes 11 and 12. In this example, the electrode 11 and the connector electrode 14 are composed of silver, and the electrode 12 and the connector electrode 15 are composed of aluminum. As one example, similar to the electrode 11, the connector electrode 14 is composed of a silver-based material, and, similar to the electrode 12, the connector electrode 15 is composed of an aluminum-based material. In accordance with this, the connector electrodes 14 and 15 can be respectively sewn into the bases 13A and 13B in a series of operations with sewing operations into the bases 13A and 13B of the electrodes 11 and 12. Any material may be used for the electrode 11 as long as it has a structure of a thread shape or a band shape and can serve as a positive electrode, and, for example, magnesium, zinc, or iron may be used. In addition, any material may be used for the electrode 12 as long as it has a structure of a thread shape or a band shape and can serve as a negative electrode, and, for example, tin, lead, copper, stainless steel, carbon, gold, or platinum may be used.

A length (width) W3 of the connector electrode 14 in the x-axis direction is larger than a length (width) W4 of the electrode 11 in the x-axis direction. In addition, a length (width) W3 of the connector electrode 15 in the x-axis direction is larger than a length (width) W5 of the electrode 12 in the x-axis direction. In accordance with this, when the module 3 is housed in the housing body 16 as will be described below, positioning of the housed module 3 for connection between the connector electrodes 31 and 32 and the connector electrodes 14 and 15 can be easily performed or becomes unnecessary.

Preferably, the density of threads sewed into the bases 13A and 13B composing the connector electrodes 14 and 15 is higher than the density of threads sewed into the bases 13A and 13B composing the connector electrodes 11 and 12. In accordance with this, when the module 3 is housed in the housing body 16 as will be described below, there is a high possibility of the connector electrodes 14 and 15 coming in contact with the connector electrodes 31 and 32 of the housed module 3. As a result, not only can positioning of the module 3 for connection between the connector electrodes 31 and 32 and the connector electrodes 14 and 15 be easily performed or unnecessary, but also contact resistance between the connector electrodes 14 and 15 and the connector electrodes 31 and 32 of the housed module 3 can be lowered.

As illustrated in FIG. 2, in the sensor 1, the electrodes 11 and 12 are respectively disposed in the bases 13A and 13B in the y-axis direction, and the connector electrodes 14 and 15 are formed at upper ends thereof. These are formed by sewing the bases 13A and 13B using threads having conductivity.

Next, the first sensor member 1A and the second sensor member 1B are disposed to overlap each other and are sewn together in a direction (the z-axis direction) orthogonal to a plane defined by the x axis and the y axis such that the shapes of the bases 13A and 13B coincide or roughly coincide with each other. In the bases 13A and 13B, seam allowances 133 are provided in edges of sides other than an uppermost side. The first sensor member 1A and the second sensor member 1B are configured to overlap each other and be fixed in accordance with sewing the seam allowances 133 together.

At this time, as illustrated in FIG. 2, the bases 13A and 13B overlap each other such that the electrodes 11 and 12 do not overlap each other. In accordance with this, the electrodes 11 and 12 are disposed by leaving a space therebetween in the x-axis direction. As a result, the sensor 1 can detect presence of a liquid between the electrodes 11 and 12 in accordance with power generation.

By sewing the bases 13A and 13B together in the seam allowances 133, as illustrated in FIG. 3, a space 16A is formed between the first base parts 131 of the bases 13A and 13B. In accordance with this, the housing body 16 can be easily configured using the space 16A as a space used for housing the module 3.

In accordance with no disposition of the seam allowance 133 on the uppermost sides of the bases 13A and 13B, when the bases 13A and 13B are sewed together in the seam allowances 133, as illustrated in FIG. 3, the uppermost sides of the bases 13A and 13B configure an opening 16B of the housing body 16. The opening 16B functions as an insertion part of the housing body 16 for the module 3. In accordance with this, as illustrated in FIG. 3, the module 3 can be easily inserted into the housing body 16 from the opening 16B.

In addition, the insertion part of the housing body 16 for the module 3 may be disposed in a part of the housing body 16 but is not limited to the uppermost side. In other words, a side on which the seam allowance 133 is not disposed among edges of the first base part 131 may be any one side in the x-axis direction. As another example, as illustrated in FIG. 4, lateral sides of the bases 13A and 13B may configure an opening 16C of the housing body 16, or both lateral sides may configure an opening 16C. Also in this case, as illustrated in FIG. 4, the module 3 can be easily inserted into the housing body 16 from the opening 16C.

In the module 3, the connector electrodes 31 and 32 are disposed on both faces including one face and a rear face side of the face. As one example, the module 3 may be a rectangular parallelepiped, and the connector electrodes 31 and 32 are disposed on two faces facing each other among six faces thereof. The connector electrodes 31 and 32 respectively function as a positive electrode and a negative electrode.

As illustrated in FIG. 3 or FIG. 4, the module 3 is housed in the housing body 16 such that the connector electrode 31, which is a positive electrode, faces the connector electrode 14 which is a positive electrode, and the connector electrode 32, which is a negative electrode, faces the connector electrode 15 which is a negative electrode. The connector electrodes 14 and 15 are sewed into the first base part 131 such that they are exposed to an inner face of the housing body 16. For this reason, the connector electrodes 31 and 32 are brought into contact with the connector electrodes 14 and 15 exposed to the inner face of the housing body 16. In accordance with this, the connector electrodes 14 and 15 are respectively connected to the connector electrodes 31 and 32 of the module 3. As a result, the electrodes 11 and 12 are respectively connected to the connector electrodes 31 and 32 of the module 3 through the connector electrodes 14 and 15 connected to ends thereof.

Since the connector electrodes 14 and 15 are sewn such that they are exposed to the inner face of the housing body 16, only by housing the module 3 in the housing body 16, the connector electrodes 14 and 15 can be easily connected to the connector electrodes 31 and 32. At this time, since the widths of the connector electrodes 14 and 15 are larger than the widths of the electrodes 11 and 12, positioning with the connector electrodes 31 and 32 becomes unnecessary or easy. In addition, since the module 3 is not exposed to the outside, damage and contamination can be prevented, and damage of connection to the connector electrodes 14 and 15 can be also prevented.

Preferably, at least one of the sensor 1 and the module 3 further includes a contact part which brings the connector electrodes 31 and 32 of the module 3 housed in the housing body 16 and the connector electrodes 14 and 15 of the inside of the housing body 16 to be in contact with each other.

FIG. 5 is a schematic diagram illustrating a specific example of the contact part. The contact part of the sensor 1 includes a pressing member which presses a module 3 housed in the housing body 16 to the inner face of the housing body 16. For example, the pressing member may be a belt 17 which is wound around the housing body 16 from the outer side. Preferably, the belt 17 is composed of an elastic material such as rubber and fixes the module 3 after housing from the outside of the housing body 16. Other than a member of an opening-rotation type such as the belt 17, the pressing member may be a member of an interposition type of a clip shape which interposes the housing body 16 therebetween from the outside, a member such as a button or a hook and loop fastener disposed inside of the housing body 16 which closes an opening 16B of the housing body 16 or may be a combination thereof.

The contact part of the module 3 is a protrusion disposed on the front face of the module 3. For example, the protrusion may be a convex part 33 disposed on a face on which the connector electrodes 31 and 32 are installed. In addition, both the sensor 1 and the module 3 may have such structures. By including a contact part in at least one of the sensor 1 and the module 3, the connector electrodes 31 and 32 of the module 3 housed in the housing body 16 and the connector electrodes 14 and 15 of the inside of the housing body 16 are brought into contact with each other. For this reason, connection of these connector electrodes is reliably formed. In addition, the connection is maintained.

Figure 6:
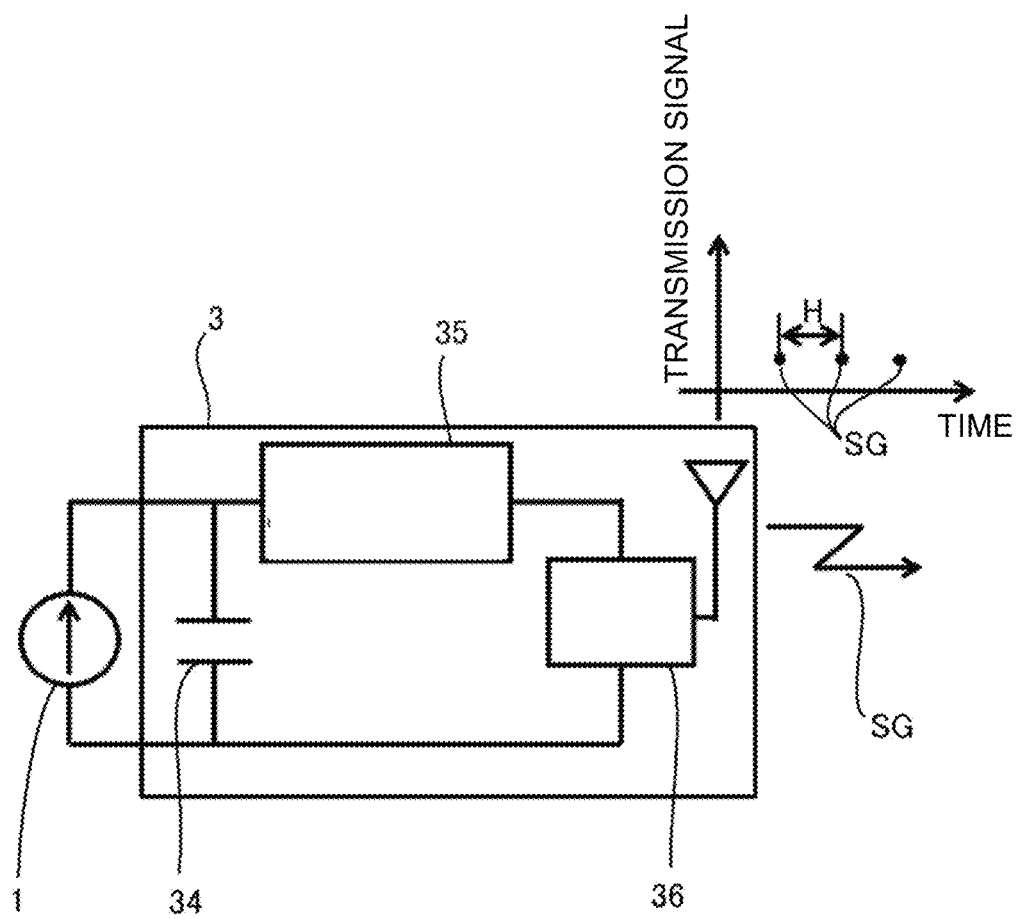
FIG. 6 is a schematic diagram illustrating a configuration of a module.

FIG. 6 is a schematic diagram illustrating a configuration of the module 3. The module 3 is a sensor module, detects power generation of the electrodes 11 and 12 included in the sensor 1, and outputs a signal representing a detection result. In more details, as illustrated in FIG. 6, the module 3 includes a capacitor 34. The capacitor 34 is connected to the sensor 1 through the connector electrodes 31 and 32 and the connector electrodes 14 and 15 and saves electric power generated using the electrodes 11 and 12. In FIG. 6, the connector electrodes 31 and 32 and the connector electrodes 14 and 15 are omitted.

The module 3 includes an intermittent power converting circuit 35. The capacitor 34 is connected to a power supply terminal of the intermittent power converting circuit 35. The intermittent power converting circuit 35 causes the capacitor 34 to operate as an operation power supply. The intermittent power converting circuit 35 monitors a charge voltage of the capacitor 34.

A radio transmitter 36 is connected to the intermittent power converting circuit 35. The radio transmitter 36 outputs a communication signal using radio communication. For example, the radio communication is Bluetooth (a registered trademark), Bluetooth Low Energy (a registered trademark), or the like.

The intermittent power converting circuit 35 detects whether the charge voltage of the capacitor 34 has reached a setting voltage set as a drive condition of the radio transmitter 36. When the reach has been detected, the intermittent power converting circuit 35 supplies electric power charged in the capacitor 34 to the radio transmitter 36. In accordance with this, a radio signal SG is output from the radio transmitter 36.

In accordance with the intermittent power converting circuit 35 supplying electric power to the radio transmitter 36, the electric power of the capacitor 34 is consumed. When the electric power is consumed, the electric potential of the capacitor 34 is lowered, and the intermittent power converting circuit 35 stops its operation. In accordance with this, supply of the electric power to the radio transmitter 36 stops. When the electrodes 11 and 12 are generating power, the capacitor 34 is charged again.

When the electrodes 11 and 12 are generating power, the capacitor 34 repeats charging and discharging. In accordance with this, output of a radio signal SG from the radio transmitter 36 becomes intermittent. Thus, the radio signal SG output from the radio transmitter 36 becomes a detection signal representing detection of a liquid present between the electrodes 11 and 12.

An output interval H of radio signals SG from the radio transmitter 36 depends on a charging speed of the capacitor 34. The larger the amount of generated power, the higher the charging speed. Thus, the larger the amount of generated power of the electrodes 11 and 12, the shorter the output interval H of radio signals SG from the radio transmitter 36. In addition, the smaller the amount of generated power, the shorter the output interval of radio signals.

The sensor 1 is disposed in a member mounted in a human body as an example and is used for detection of presence/absence of a liquid in the member. For example, the member mounted in the human body is a diaper. By disposing the sensor 1 in a member mounted in a human body, the housing body 16 is also disposed in the member. For this reason, the module 3 can be inserted into the member mounted in a human body. In accordance with this, presence/absence of a liquid in a member mounted in a human body can be detected using a wearable device.

Figure 7:
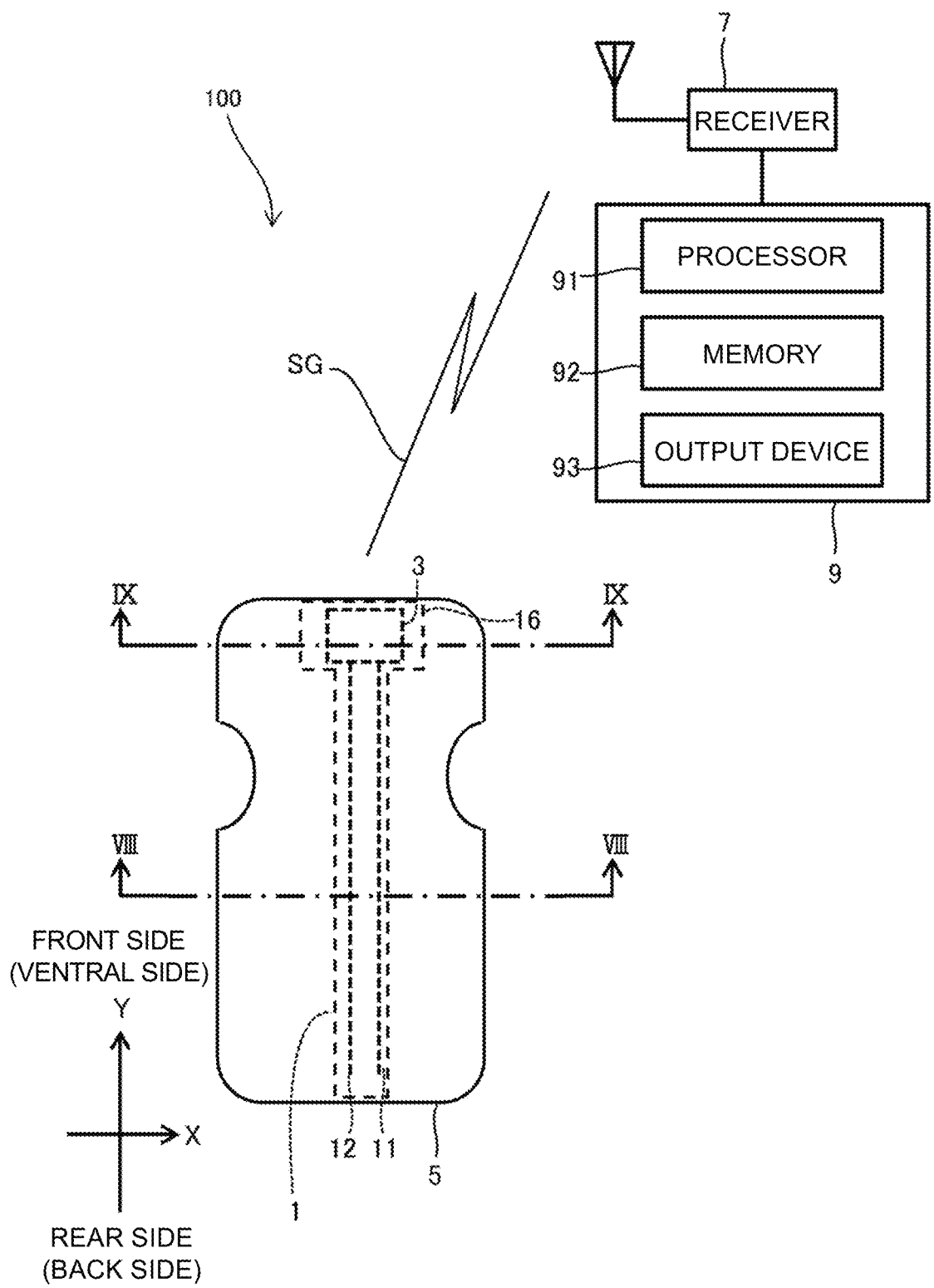
FIG. 7 is a schematic diagram illustrating an overview of a case in which a sensor is used in a detection system.
Figure 8:
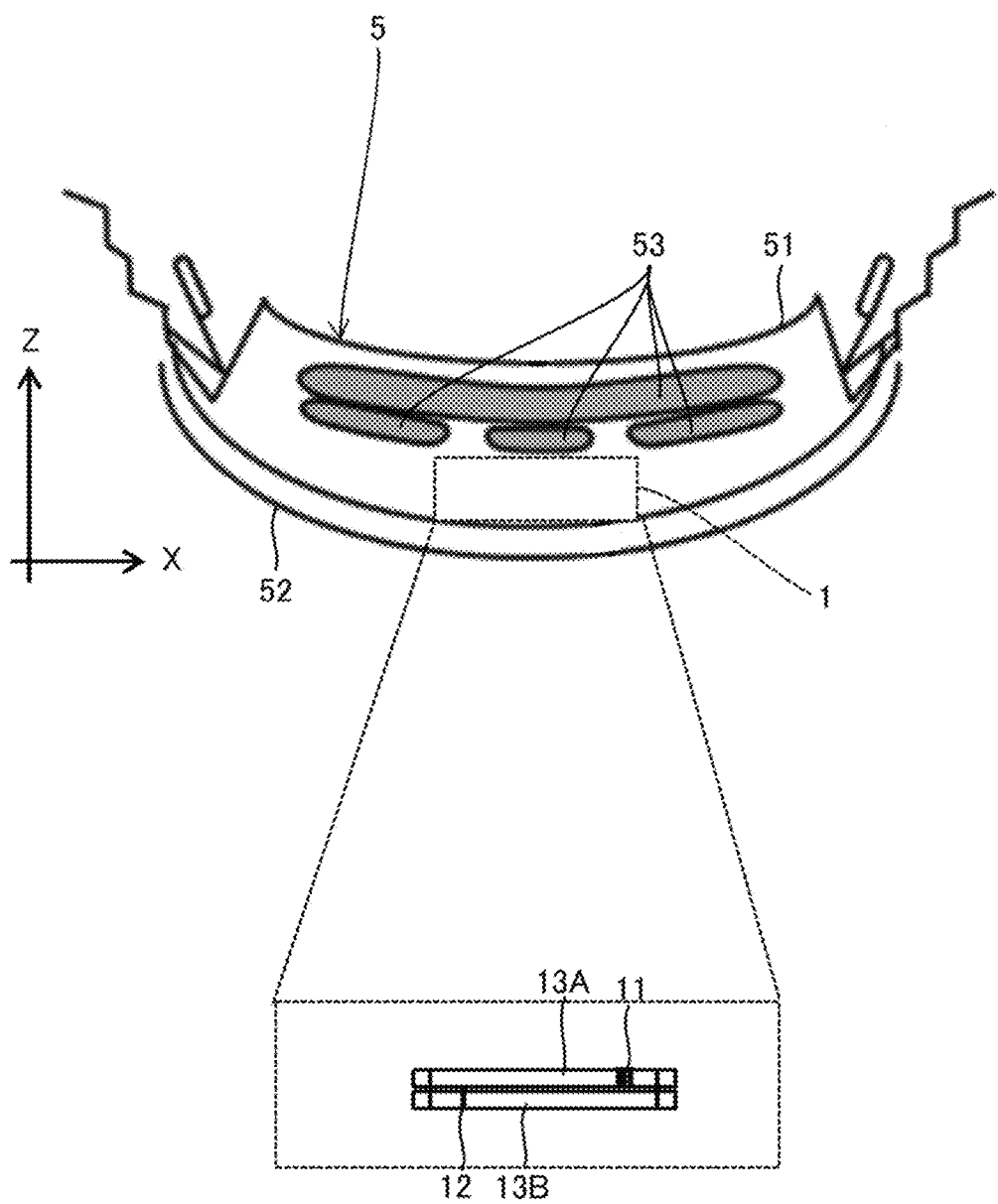
FIG. 8 is a cross-sectional view of an absorption member main body along line VIII-VIII illustrated in FIG. 7.
Figure 9:
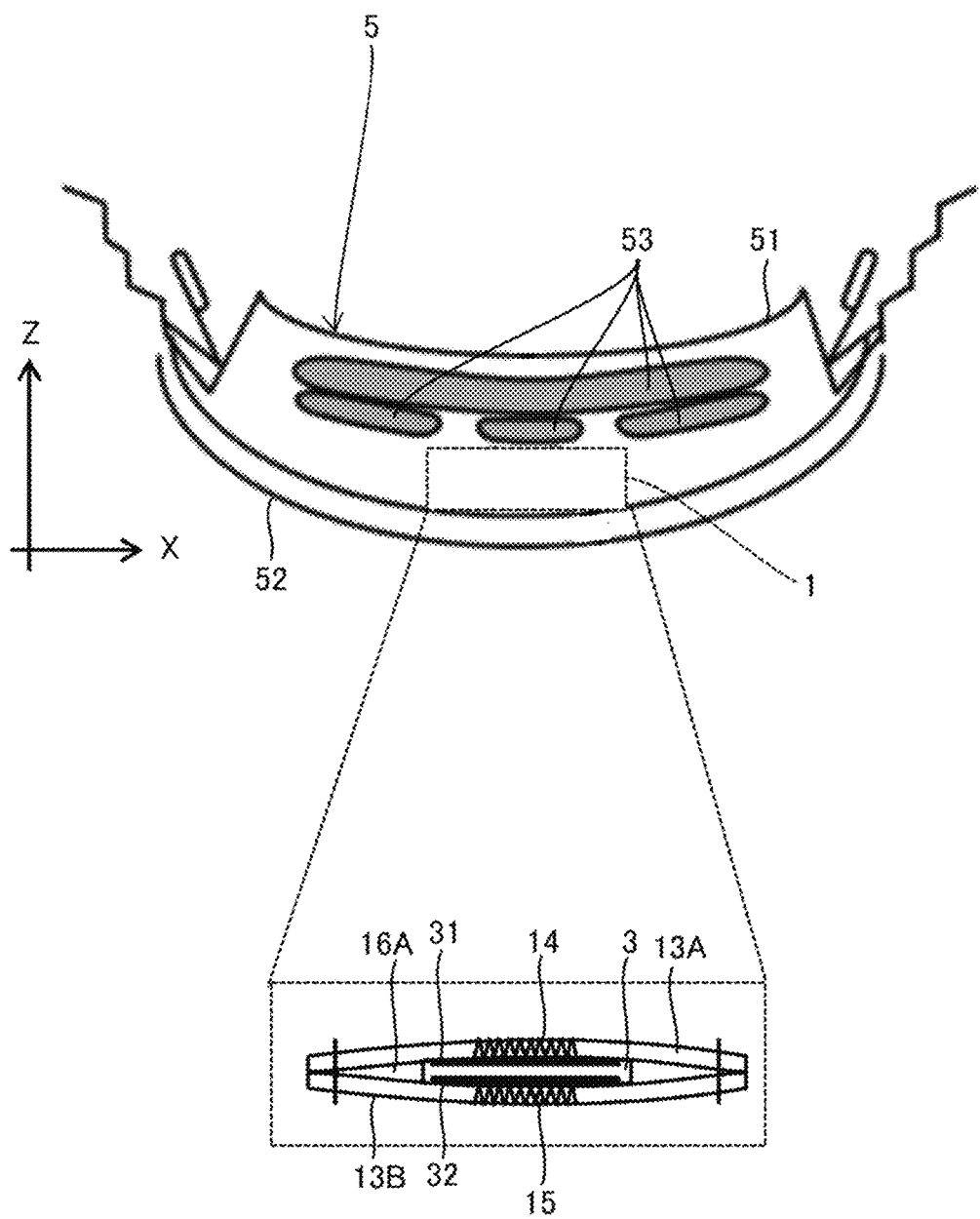
FIG. 9 is a cross-sectional view of an absorption member main body along line IX-IX illustrated in FIG. 7.

FIG. 7 is a schematic diagram illustrating an overview of a case in which the sensor 1 is disposed in the absorption member main body 5 as an example of a member mounted in a human body and is used in a detection system 100 detecting presence/absence of a liquid in the absorption member main body 5. The detection system 100 detects a liquid present in the absorption member main body 5 using the sensor 1 installed in the absorption member main body 5. FIG. 8 is a cross-sectional view of the absorption member main body 5 taken along line VIII-VIII illustrated in FIG. 7. FIG. 9 is a cross-sectional view of the absorption member main body 5 taken along line IX-IX illustrated in FIG. 7. The absorption member main body 5 has a basic configuration as a diaper as an example.

The absorption member main body 5 has an almost rectangular shape which is long in one direction in the plan view in an expanded state. In the absorption member main body 5, a length direction will be defined as a Y axis, a lateral direction orthogonal to the length direction will be defined as an x axis, and a direction orthogonal to those will be defined as a Z axis. The Y-axis direction coincides with a front-back direction at the time of mounting the absorption member main body in a mounting person. In other words, a position having a large positive value among positions in the Y-axis direction will be referred to as a front side, and a position having a large negative value will be referred to a rear side. The X-axis direction coincides with the width direction. The Z-axis direction coincides with a vertical direction at the time of mounting, a positive direction of the Z axis is an upward direction and a side toward a mounting person at the time of mounting the absorption member main body in the mounting person, and a negative direction of the Z axis is a downward direction and a side toward an outer side at the time of downwardly mounting the absorption member main body in the mounting person.

The absorption member main body 5 includes a front sheet 51, a rear sheet 52, and an absorption body 53. The absorption body 53 is disposed between the front sheet 51 and the rear sheet 52. A front face of the absorption member main body 5 represents a face of a side brought into contact with a mounting person when the absorption member main body 5 is mounted in the mounting person. Thus, excrement of the mounting person is given from the front sheet 51 side to the absorption body 53.

The front sheet 51 is a liquid transmissive sheet having an approximately rectangular shape. For example, the front sheet 51 is formed using a nonwoven fabric or a woven fabric. The front sheet 51 is brought into contact with a skin of a mounting person when the absorption member main body is mounted in the mounting person. The front sheet 51 is configured such that a transmitted liquid is difficult to turn back to the mounting person side by improving transmissivity of the liquid. In accordance with this, urine excreted from the mounting person can be quickly transmitted to the absorption body 53. Thus, even when there is excretion, as long as there is remaining power in an absorption capability of the absorption body 53, the front sheet 51 does not substantially hold urine and is in a substantially dry state. As a result, urine is inhibited from being brought into contact with the skin of the mounting person.

The rear sheet 52 is a non-liquid transmissive sheet having an approximately rectangular shape. The rear sheet 52 is formed using a water-proof member having a water-proof film or the like. The rear sheet 52 prevents urine absorbed by the absorption body 53 from leaking to the outside.

The absorption body 53 is composed of an absorptive fiber such as a pulp and a high-absorbent polymer. In accordance with the high-absorbent polymer, much liquid can be held by the absorption body 53. The absorption body 53 is a mat body having an approximately rectangular shape which is long in one direction. The absorption body 53 has a longitudinal direction which approximately coincides with the Y-axis direction of the absorption member main body 5 and is disposed over a front side and a rear side of the absorption member main body 5. Thus, together with absorbing urine excreted on the front side, the absorption body 53 can absorb urine exceeding the amount of absorption of the front side on the rear side.

The sensor 1 is disposed between the absorption body 53 and the rear sheet 52. In other words, the sensor 1 is disposed on a rear sheet 52 side of the absorption body 53. The sensor 1 functions as a urine power generation battery.

The sensor 1 is disposed in the absorption member main body 5 with positive/negative directions of the Y-axis direction approximately coinciding with positive/negative directions of the Y-axis direction of the absorption member main body 5. Thus, the electrodes 11 and 12 are disposed along the Y-axis direction apart from the absorption member main body 5 in the X-axis direction.

FIG. 8 illustrates a cross-section of the sensor 1 on the rear side of the absorption member main body 5 in which the sensor 1 is disposed, and FIG. 9 illustrates a cross-section of the sensor 1 at the position of the housing body 16 on the front side. Referring to FIG. 8, on the rear side of the absorption member main body 5, the electrodes 11 and 12 are disposed apart from each other in the X-axis direction.

Referring to FIG. 9, on the rear side of the absorption member main body in a space 16A between bases 13A and 13B composing the housing body 16, the module 3 is housed such that the connector electrodes 31 and 32 are respectively brought into contact with the connector electrodes 14 and 15 disposed in the housing body 16.

The sensor 1 is disposed in the absorption member main body 5 such that the bases 13A and 13B overlapping each other are brought into contact with the rear sheet 52 side of the absorption body 53.

Since the bases 13A and 13B overlapping each other are disposed with being brought into contact with the absorption body 53, a liquid absorbed by the absorption body 53 moves to the bases 13A and 13B overlapping each other. The bases 13A and 13B which have absorbed a liquid from the absorption body 53 overlapping each other become a path for generation of a current between the electrodes 11 and 12. For this reason, in accordance with the electrodes 11 and 12 being brought into contact with a liquid which has been absorbed by the absorption body 53, a current is generated. In accordance with this, the sensor 1 is used for detection of liquid absorption of the absorption body 53.

The larger an area in which the electrodes 11 and 12 are brought into contact with a liquid, the larger the amount of generated power. In other words, the electrodes 11 and 12 are disposed to be brought into contact with the absorption body 53 with the longitudinal direction approximately coinciding with the longitudinal direction of the absorption body 53, and thus the more amount of a liquid absorbed in the absorption body 53, the larger the amount of generated power. Thus, as illustrated in FIG. 6, the output interval H of radio signals SG from the radio transmitter 36 represents an amount of liquid absorbed by the absorption body 53.

As illustrated in FIG. 7, the detection system 100 may include a receiver 7. The receiver 7 receives a radio signal SG transmitted from the radio transmitter 36. The receiver 7 may be connected to a management device 9. Reception data is given to the management device 9 from the receiver 7. The management device 9 is a computer including a processor 91 and a memory 92 and, as an example, may be a terminal device such as a smartphone.

By executing a program stored in the memory 92, the processor 91 can perform a process relating to a degree of absorption of the absorption body 53 of the absorption member main body 5. For example, the process relating to the degree of absorption of the absorption body 53 of the absorption member main body 5 is a process of determining necessity/unnecessity of replacement of the diaper. When the liquid reaches the rear side of the absorption body 53, the absorption member main body 5 determines a replacement time. In a case in which it is determined that replacement of the diaper is necessary, the output device 93 of the management device 9 outputs necessity of the replacement of the diaper.

The inventors and the like performed a test for evaluating sensing of the sensor 1 according to this embodiment. In the test, after the sensor 1 was disposed in the absorption member main body 5, and 600 ml of liquid is injected into the absorption member main body 5, presence/absence of reception of a radio signal SG in the receiver 7 was measured, and measurement results illustrated in FIG. 10 were acquired. A vertical axis represents presence/absence of reception of a radio signal SG, "0" represents absence of reception, and "1" represents presence of reception. A horizontal axis represents an elapse time after injection of 600 ml of liquid into the absorption member main body 5. Thus, the measurement results illustrated in FIG. 10 represent timings at which a radio signal SG is received after injection of illiquid using an elapse time from injection of the liquid.

Figure 10:
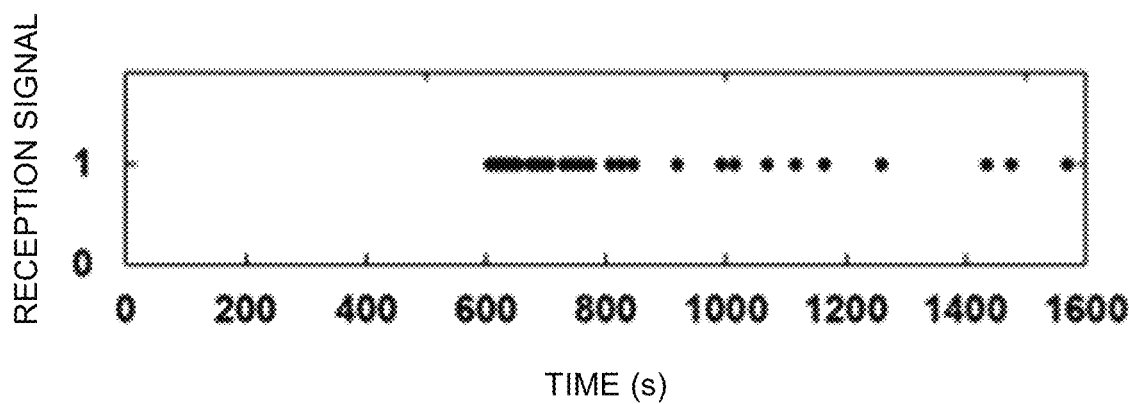
FIG. 10 is a diagram illustrating results of measurements of wireless signals acquired through the inventors' tests of a detection system.

From the results illustrated in FIG. 10, reception of a radio signal SG starts at a timing at which 600 seconds elapses after injection of liquid. In other words, it can be understood that, in a case in which 600 ml of liquid is injected into the absorption member main body 5, by using the sensor 1, the liquid is detected after 600 seconds.

The present invention is not limited to the embodiment described above, and various modifications can be made. In the embodiment described above, although urine has been described as an example of liquid, the liquid is not limited to the urine, and various kinds of liquid can be detected as long as the liquid generates power in the electrodes by being brought into contact with the electrodes. The sensor can be used as a water leakage sensor or a rainwater sensor.

What is claimed is:

1. A power generation sensor generating electric power using a liquid, the power generation sensor comprising:
   a base;
   a positive electrode for power generation disposed in a first direction of the base and composed of a first material;
   a negative electrode for power generation disposed in the first direction of the base and composed of a second material;
   a first connector electrode connected to a one-side end of the positive electrode in the first direction and connected to a sensor module; and
   a second connector electrode connected to a one-side end of the negative electrode in the first direction and connected to the sensor module,
   wherein the first connector electrode is composed of the first material and has a width in a second direction orthogonal to the first direction larger than a width of the positive electrode in the second direction, and
   wherein the second connector electrode is composed of the second material and has a width in the second direction larger than a width of the negative electrode in the second direction.

2. The power generation sensor according to claim 1,
   wherein each of the positive electrode and the negative electrode is composed of a thread having conductivity sewn into the base, and
   wherein each of the first connector electrode and the second connector electrode is composed of a thread sewn into a range of the base wider than the positive electrode and the negative electrode.

3. The power generation sensor according to claim 2, wherein densities of the threads which compose the first connector electrode and the second connector electrode sewn into the base are higher than densities of the threads which compose the positive electrode and the negative electrode sewn into the base.

* * * * *